United States Patent
Joshi et al.

(10) Patent No.: US 10,696,468 B2
(45) Date of Patent: *Jun. 30, 2020

(54) GAS CELL DRIVEN FLUID DELIVERY DEVICE FOR SPILL-RESISTANT STORAGE AND USE

(71) Applicant: Microlin, LLC, Salt Lake City, UT (US)

(72) Inventors: Ashok V. Joshi, Salt Lake City, UT (US); John H Gordon, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 298 days.

This patent is subject to a terminal disclaimer.

(21) Appl. No.: 15/721,942

(22) Filed: Oct. 1, 2017

(65) Prior Publication Data

US 2018/0022532 A1 Jan. 25, 2018

Related U.S. Application Data

(63) Continuation-in-part of application No. 15/396,759, filed on Jan. 2, 2017, now Pat. No. 10,183,091, which
(Continued)

(51) Int. Cl.
*B65D 83/00* (2006.01)
*B05B 11/04* (2006.01)
(Continued)

(52) U.S. Cl.
CPC ............ *B65D 83/0072* (2013.01); *A61L 9/12* (2013.01); *A61M 5/1483* (2013.01);
(Continued)

(58) Field of Classification Search
CPC ............ A61M 5/14593; A61M 5/1483; A61M 5/155; A61M 2005/14204; B65D 83/62;
(Continued)

(56) References Cited

U.S. PATENT DOCUMENTS 3,159,176 A * 12/1964 Russell .................... B60T 11/28
137/493.1
3,471,349 A 10/1969 Cohen
(Continued)

OTHER PUBLICATIONS

Ahn, Yae Y, Written Opinion of the International Searching Authority, PCT Application No. PCT/US2003/056662 (corresponding to U.S. Appl. No. 14/010,242 (dated Nov. 25, 2013), 1-8.
(Continued)

*Primary Examiner* — Alex M Valvis
(74) *Attorney, Agent, or Firm* — Brian C. Trask

(57) ABSTRACT

An orientation independent delivery device including a replaceable cartridge that may be installed on a foundation. A cartridge includes a gas chamber, a delivery chamber, a gas cell, and a delivery aperture. The gas chamber includes a gas-side rigid portion and a gas-side flexible barrier. The gas-side flexible barrier is sealed to the gas-side rigid portion. The delivery chamber includes a delivery-side rigid portion and a delivery-side flexible barrier. The delivery-side flexible barrier is sealed to the delivery-side rigid portion and is oriented adjacent to the gas-side flexible barrier. The gas cell is coupled to the gas-side rigid portion of the gas chamber. The gas cell increases a gas pressure within the gas chamber to expand the gas-side flexible barrier. Expansion of the gas-side flexible barrier applies a compressive force to the delivery-side flexible barrier allowing a delivery material to escape from the delivery chamber.

18 Claims, 14 Drawing Sheets

Related U.S. Application Data is a continuation-in-part of application No. 14/632,970, filed on Feb. 26, 2015, now Pat. No. 9,533,066, and a continuation-in-part of application No. 14/537,691, filed on Nov. 10, 2014, now Pat. No. 9,623,135, which is a continuation-in-part of application No. 15/485,206, filed on Apr. 11, 2017, now Pat. No. 10,399,102, which is a continuation-in-part of application No. 14/010,242, filed on Aug. 26, 2013, now Pat. No. 9,840,361.

(60) Provisional application No. 61/944,698, filed on Feb. 26, 2014, provisional application No. 61/902,031, filed on Nov. 8, 2013, provisional application No. 61/692,750, filed on Aug. 24, 2012.

(51) Int. Cl.
| | | |
|---|---|---|
| *B05B 11/00* | (2006.01) | |
| *A61M 5/145* | (2006.01) | |
| *A61M 5/148* | (2006.01) | |
| *A61M 5/155* | (2006.01) | |
| *A61M 5/142* | (2006.01) | |
| *A61L 9/12* | (2006.01) | |

(52) U.S. Cl.
CPC ........ *A61M 5/14593* (2013.01); *A61M 5/155* (2013.01); *B05B 11/0059* (2013.01); *B05B 11/00412* (2018.08); *B05B 11/046* (2013.01); *B05B 11/3028* (2013.01); *A61M 2005/14204* (2013.01)

(58) Field of Classification Search
CPC . B65D 83/625; B05B 11/046; B05B 11/0059; B05B 11/3028; B05B 11/00412; A61L 9/12

USPC ....... 604/141, 145; 222/386.5, 389; 204/266
See application file for complete search history.

(56) References Cited

U.S. PATENT DOCUMENTS

| | | | |
|---|---|---|---|
| 3,504,827 A | | 4/1970 | Larson |
| 3,940,032 A | | 2/1976 | Gershon |
| 3,945,539 A | | 3/1976 | Sassong |
| 4,358,026 A | | 11/1982 | Makinen |
| 5,090,963 A | * | 2/1992 | Gross .................... A61M 5/155 604/132 |
| 5,354,264 A | * | 10/1994 | Bae ........................ A61M 5/155 604/21 |
| 5,398,851 A | * | 3/1995 | Sancoff ............. A61M 5/14593 222/386.5 |
| 5,399,166 A | | 3/1995 | Laing |
| 5,573,646 A | | 11/1996 | Saito et al. |
| 5,738,657 A | | 4/1998 | Bryant |
| 5,744,014 A | | 4/1998 | Gordon et al. |
| 5,899,381 A | | 5/1999 | Gordon et al. |
| 7,681,809 B2 | * | 3/2010 | Maget ................. A01M 1/2044 222/187 |
| 2012/0060947 A1 | | 3/2012 | Reichert |
| 2013/0095225 A1 | * | 4/2013 | Lebaron ................ A23L 3/0155 426/665 |

OTHER PUBLICATIONS

Extended European Search report, PCT Application No. PCT/US2003/056662 (corresponding to U.S. Appl. No. 14/010,242, dated Mar. 31, 2016.

\* cited by examiner

GAS CELL DRIVEN FLUID DELIVERY DEVICE FOR SPILL-RESISTANT STORAGE AND USE

RELATED APPLICATIONS

This application is a continuation-in-part of U.S. Utility patent application Ser. No. 15/485,206, filed Apr. 11, 2017 and titled "SPILL-RESISTANT FLUID DELIVERY DEVICE", which is a continuation-in-part of U.S. Utility patent application Ser. No. 14/010,242, filed Aug. 26, 2013 and titled "GAS CELL DRIVEN ORIENTATION INDEPENDENT DELIVERY DEVICE", which claims the benefit of the filing date of U.S. Provisional Application Ser. No. 61/692,750, filed Aug. 24, 2012; and is a continuation-in-part of U.S. Utility patent application Ser. No. 15/396,759, filed Jan. 2, 2017 and titled "NO-DRIP VOLATILE SUBSTANCE DELIVERY SYSTEM", which is a continuation-in-part of U.S. Utility patent application Ser. No. 14/632,970, filed on Feb. 26, 2015, now U.S. Pat. No. 9,533,066, issued Jan. 3, 2017 and titled "VOLATILE SUBSTANCE DELIVERY SYSTEM, which claims the benefit of the filing date of U.S. Provisional Application Ser. No. 61/944,698, filed on Feb. 26, 2014, and is a continuation-in-part of U.S. Utility patent application Ser. No. 14/537,691, filed Nov. 10, 2014 and titled "VOLATILE SUBSTANCE DELIVERY SYSTEM", which claims the benefit of the filing date of U.S. Provisional Application Ser. No. 61/902,031, filed on Nov. 8, 2013, the disclosures of all of which are hereby incorporated in their entirety by this reference as though set forth herein.

BACKGROUND

Field of the Invention

This invention relates to pumps and devices configured to dispense controlled amounts of fluid. It is particularly directed to spill-resistant fluid delivery systems.

Background

Liquid and gas delivery systems serve many roles in many different fields from medical treatment devices to air fresheners. Frequently, conventional delivery systems involve some variety of a pump. Many different types of pumps exist with different strengths and weaknesses.

For example, some pumps are orientation sensitive. These pumps must be aligned or situated within certain thresholds to function properly. Other pumps require large amounts of operating force to move small amounts of material. Some pumps are susceptible to debris and particulate matter within a fluid stream.

SUMMARY

An embodiment according to certain principles of the invention forms an orientation independent fluid delivery device. A currently preferred embodiment includes a foundation and a cartridge. A workable foundation may be configured for disposition in association with a surface of a local environment. A foundation may be substantially permanent, such as by being affixed to a wall, or may be carried on a table or other temporary support surface.

A retention mechanism is provided to hold the cartridge in installed registration with respect to the foundation and to permit removal of the cartridge from the foundation for replacement of the cartridge with a replacement cartridge. A retention mechanism can include a toggle clamping mechanism. Another operable retention mechanism includes an inclined plane with a cooperating captured element, wherein the mechanism is operated by rotation of the cartridge with respect to the foundation. For non-limiting example, a groove having a lead can capture a portion of a thread or tang such that rotation of the foundation with respect to the cartridge draws the elements together.

A workable cartridge includes a gas chamber with a gas-side rigid portion and a gas-side flexible barrier element. Sometimes, the gas-side flexible barrier element is permanently sealed, around a first perimeter of the gas chamber, to the gas-side rigid portion such that gas introduced to the gas chamber is confined between the gas-side flexible barrier element and the gas-side rigid portion.

A cartridge may also include a delivery chamber with a delivery-side rigid portion and a delivery-side flexible barrier element. Sometimes, the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion. The delivery-side flexible barrier element is typically oriented adjacent to, and is a distinct element from, the gas-side flexible barrier element. In preferred embodiments, the gas-side flexible barrier element has an outer surface that is in continuous direct contact with the delivery-side flexible barrier element without separation.

A gas cell is associated with the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element. The foundation and the cartridge may be structured cooperatively to place the gas cell into operational gas-generating mode by the act of coupling the cartridge to the foundation. Certain embodiments may include keeper means to maintain the gas cell in a loose and venting association with a gas-side rigid portion of a cartridge during storage and transport of the cartridge prior to placing the device into use to dispense material.

The delivery chamber includes a delivery aperture to allow a portion of delivery material to escape from the delivery chamber in response to deflection of the delivery-side flexible barrier element in a direction toward the delivery-side rigid portion. Typically, an emanator is associated with the delivery aperture, the emanator being structured to absorb delivery material and facilitate distribution and evaporation of the delivery material over a larger area for dispersal as a vapor into a local environment. Also, an overflow emanator chamber may be associated with the delivery aperture to receive and confine small quantities or even excessive drops of delivery material. In that case, it is preferred for the overflow emanator chamber to be structured to hold a volume that is at least about half the volume held in a full delivery chamber.

Preferred embodiments include means to vent passive gas generated by the gas cell and thereby to resist spill of delivery material from the delivery device to the environment. A first workable means to vent passive gas includes a temporary vent path disposed between the gas cell and the gas-side rigid portion, the temporary vent path being formed by structure arranged to be occluded by the act of assembly of the cartridge to the base. Another means to vent passive gas comprises a passive gas-relief valve disposed in a venting association with the gas chamber to permit discharge of passive gas from inside the gas chamber to the environment.

An exemplary passive gas-relief valve includes a pore passing through the gas-side rigid portion, the pore being sized in a cross-section to throttle gas flow there-through to a rate sufficient to release passive gas, but lower than a rate required to reduce or compromise operational pressure caused by a gas cell disposed in an operating gas-generation mode. Another exemplary passive gas-relief valve includes an aperture passing through the gas-side rigid portion and a membrane disposed to resist gas flow from the gas chamber through the aperture, the membrane being sized in thickness and permeability to cooperate with a cross-section flow area defined by the aperture such that gas flow through the aperture is restricted to an escape flow rate that permits escape of passive gas, but is lower than a rate required to compromise operational pressure caused by a gas cell disposed in an operating gas-generation mode. A passive gas-relief valve in one workable embodiment is structured to restrict gas flow there-through to an escape gas flow rate of less than about 0.1 cc per day. In certain cases, a passive gas-relief valve may be structured to restrict gas flow there-through to an escape gas flow rate of between about 0.2 and about 0.5 cc per day.

Certain embodiments may include a threshold pressure valve disposed to resist undesired discharge of delivery material from the delivery chamber and through the delivery aperture.

Sometimes, an absorbent element may be disposed to facilitate completely filling the delivery chamber with delivery material during manufacture of a device to avoid presence of gas bubbles remaining in the delivery chamber.

A currently preferred orientation independent delivery device includes a foundation and a cartridge. The foundation is configured for disposition in association with a surface of a local environment and for removable coupling to the cartridge to permit replacement of the cartridge with a replacement cartridge. Importantly, the delivery device is structured to resist causing damage to the environment by way of undesired discharge of delivery material from the cartridge.

The cartridge includes a gas chamber and a delivery chamber. The chambers include rigid portions that are separated by respective flexible membrane barrier elements. A self-powered gas cell is coupled to the gas-side rigid portion of the gas chamber, and is operable to increase a gas pressure within the gas chamber to expand the gas-side flexible barrier element, wherein expansion of the gas-side flexible barrier element applies a compressive force to the delivery-side flexible barrier element. A delivery aperture communicates to the delivery chamber to allow a delivery material to escape from the delivery chamber in response to deflection of the delivery-side flexible barrier element in a direction toward the delivery-side rigid portion.

The delivery device includes means to resist spill of delivery material from the apparatus to the environment due to change in temperature or during long-term storage of a cartridge. One means to resist spill includes structure forming a vent for passive gas, the vent being configured to resist build-up of pressure in the gas chamber and caused by passive gas released from the gas cell. Another means to resist spill includes overflow mitigation structure to mitigate an effect on the local environment of undesired release of fluid from the fluid chamber. An exemplary mitigation structure includes an overflow emanator chamber associated with the delivery aperture to receive and confine spilled drops of delivery material, the emanator storage chamber having a volume at least half as large as the delivery chamber volume. Yet another means to resist spill includes bubble-avoiding structure to resist presence of gas bubbles inside an assembled and loaded material delivery chamber of a cartridge.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

In the drawings, which illustrate what are currently considered to be the best modes for carrying out the invention.

Throughout the description, similar reference numbers may be used to identify similar elements.

DETAILED DESCRIPTION OF THE ILLUSTRATED EMBODIMENTS

Figure 1:
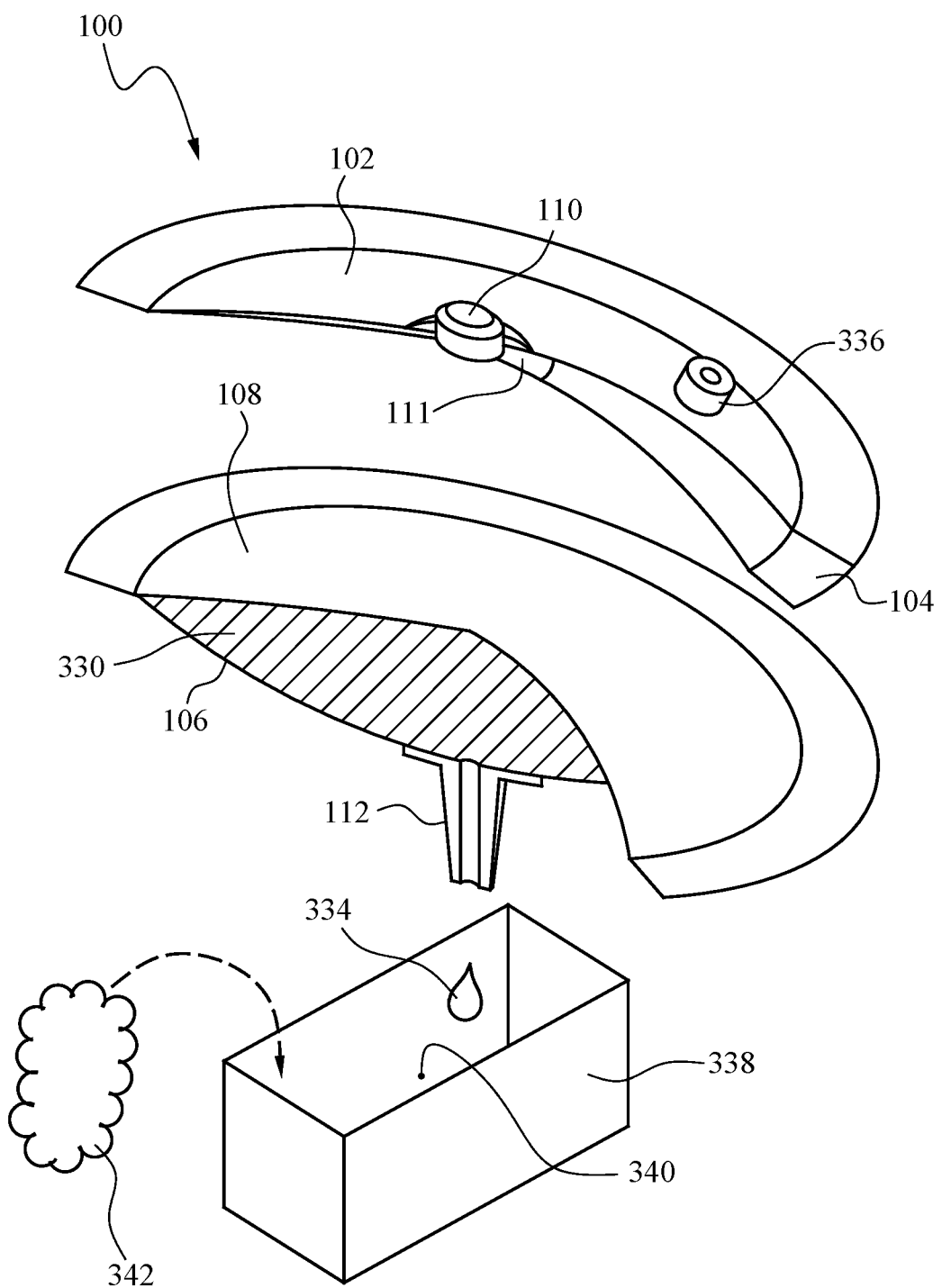
FIG. 1 depicts an exploded cut-away view in perspective of one embodiment of a delivery device.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments relate to a gas cell pump. Certain embodiments described below are drawn to delivery of a delivery material through mechanical pressure generated by a gas cell. Some embodiments may be useful to deliver medicines, scents, chemical agents, lubricants, saline, or other materials, chemicals, or chemical mixtures. In some embodiments, the pump may deliver the material to a local area. In other embodiments, the pump may deliver the material to a stream of material to yield a certain result at a near or relatively distant site. In another embodiment, the pump delivers the material at a sustained rate. For example, the pump may operate at a relatively slow rate of delivery or at a high rate. In other embodiments, the pump delivers the material at a variable rate.

In some embodiments, the pump can be loaded with a volatile and/or corrosive material for delivery. The pump can be built with materials that are specifically resistant to the particular chemical or agent that will be delivered by the pump. Additionally, some embodiments may incorporate materials that have a low permeability relative to the delivery agent. In this way, some embodiments may be specifically built to deliver a particular substance. Other embodiments may be built to handle a wide range of substances with varying corrosion and permeability characteristics.

In some embodiments, the components of the pump may be sealed together into a single unified piece. In other embodiments, some components may be joined in a manner that allows those components to be removed without damage to the pump or use of complex processes. For example, in some embodiments, the portion containing the delivery material may be removed to replace a spent portion with a new portion. In other embodiments, other portions may be removable.

In some embodiments, the pump is operable in any orientation. In other words, the pump is not sensitive to any particular orientation threshold. For example, the pump may be positioned to dispense a delivery material upwards, downwards, or at any angle in between.

FIG. 1 depicts an exploded cut-away view of one embodiment of a delivery device or pump 100. The illustrated embodiment includes a gas-side rigid portion 102, a gas-side flexible barrier 104, a delivery-side rigid portion 106, a delivery-side flexible barrier 108, a gas cell 110, and a delivery aperture 112. In the depicted embodiment, the gas-side rigid portion 102 is a domed geometry with a flanged edge. The structure of the gas-side rigid portion 102 corresponds with the structure of the gas-side flexible barrier 104. This allows the gas-side rigid portion 102 and the gas-side flexible barrier 104 to match up and form a seal. In other embodiments, the gas-side rigid portion 102 may have a different geometry than illustrated. For example, the gas-side rigid portion 102 may have a deeper curvature, it may be cylindrical or spherical, it may have planar portions or be cuboidal, and it may have a concave geometry rather than the convex geometry shown in FIG. 1.

In the pump embodiment 100 illustrated in FIG. 1, the gas-side rigid portion 102 has a smooth surface. In other embodiments, the gas-side rigid portion 102 has a surface treatment. For example, the surface treatment may include polishing, texturing, added structural elements to increase rigidity or provide some other functionality. In the depicted embodiment, the gas-side rigid portion 102 is made of a relatively rigid material. For example, the gas-side rigid portion 102 may be made of hard plastic, metal, composite, or some other rigid material.

In the embodiment 100 of FIG. 1, the gas-side flexible barrier 104 is coupled with the gas-side rigid portion 102. In some embodiments, the gas-side flexible barrier 104 is sealed to the gas-side rigid portion 102. For example, the gas-side flexible barrier 104 and the gas-side rigid portion 102 may be joined by thermal sealing, mechanical sealing, chemical sealing or adhesion, vacuum sealing, or a combination of several forms of sealing or creating a seal.

In some embodiments, the gas-side flexible barrier 104 is a flexible membrane that operates like a diaphragm. As the gas cell 110 generates gas, the gas-side flexible membrane 104 flexes to form a chamber between the gas-side flexible barrier 104 and the gas-side rigid portion 102. As the gas cell 110 continues to generate gas, the gas-side flexible barrier continues to flex to provide additional capacity within the chamber. In some embodiments, the material used for the gas-side flexible barrier 104 may be selected to have a high degree of resistance to reactivity with the gas generated by the gas cell 110. Additionally, the gas-side flexible barrier 104 may be selected to provide a low degree of permeability relative to the gas generated by the gas cell 110. In some embodiments, a material may be selected for both chemical reactivity and permeability. In other embodiments, additional qualities and characteristics may influence material selection for the gas-side flexible barrier 104. Materials which might be used either alone or in combination include acrylonitrile, methyl acrylate copolymer, poly ethylene terephthalate (PET), high density polyethylene (HDPE), also laminates such as biaxial aliphatic polyamides (also known as Nylon), aluminum foil, and low density polyethylene.

In some embodiments, the gas-side flexible barrier 104 is flexible throughout its entirety. In other embodiments, the gas-side flexible barrier 104 includes some rigid or relatively less-flexible portions incorporated within the gas-side flexible barrier 104. In some embodiments, the gas-side flexible barrier 104 has portions with varying degrees of flexibility. For example, the gas-side flexible barrier 104 may have a small rigid portion 111 that prevents the gas-side flexible barrier 104 from contacting the gas cell 110 when the gas-side flexible barrier 104 is fully collapsed against the gas-side rigid portion 102. Other embodiments incorporate other structural elements within the gas-side flexible barrier 104 to provide other functionality.

In some embodiments, the delivery-side rigid portion 106 is similar to the gas-side rigid portion 102. In other embodiments, the delivery-side rigid portion 106 is unique in form and functionality. For example, the delivery-side rigid portion 106 may be formed to improve the flow of delivery material to the delivery aperture 112 or may include a refill interface (not shown). Other functionality and structure may be included in other embodiments. In some embodiments, the delivery-side rigid portion 106 matches the form of the gas-side rigid portion 102 where they meet to facilitate sealing the delivery side (e.g., 116 of FIG. 4) and the gas side (e.g., 114 of FIG. 4) together. In other embodiments, the delivery-side rigid portion 106 varies in geometry from the gas-side rigid portion 102.

In the embodiment 100 depicted in FIG. 1, the delivery-side flexible barrier 108 is coupled to the delivery-side rigid portion 106. In some embodiments, the delivery-side flexible barrier 108 is formed of material with a high degree of chemical resistance relative to a delivery material. In other embodiments, the delivery-side flexible barrier 108 also has a low degree of permeability relative to the delivery material. In some embodiments, the delivery-side flexible barrier 108 has a high degree of permeability relative to the gas generated by the gas cell 110. This would allow any stray gas from the gas cell 110 that has collected on the delivery side 116 to escape through the delivery-side flexible barrier 108 without forming a bubble or otherwise affecting the delivery side 116 of the device 100. In some embodiments, similar gas venting functionality is incorporated into the delivery-side rigid portion 106.

In the device illustrated in FIG. 1, the gas cell 110 is disposed in the structure of the gas-side rigid portion 102. In some embodiments, the gas cell 110 is disposed in the structure of the gas-side rigid portion 102 by application of a glass bead, silicon bead, cyanoacrylate adhesive or other form of sealant or adhesive material or process. In some embodiments, the gas cell 110 may be located at a remote site and be connected by channels or tubes to direct the gas generated by the gas cell 110 through the gas-side rigid portion 102. The gas cell 110 produces a gas and directs the gas into the area between the gas-side rigid portion 102 and the gas-side flexible barrier 104. The buildup of the gas in this area forces the gas-side flexible barrier 104 to move away from the gas-side rigid portion 102. This provides the driving forces for operation of the device.

Figure 10:
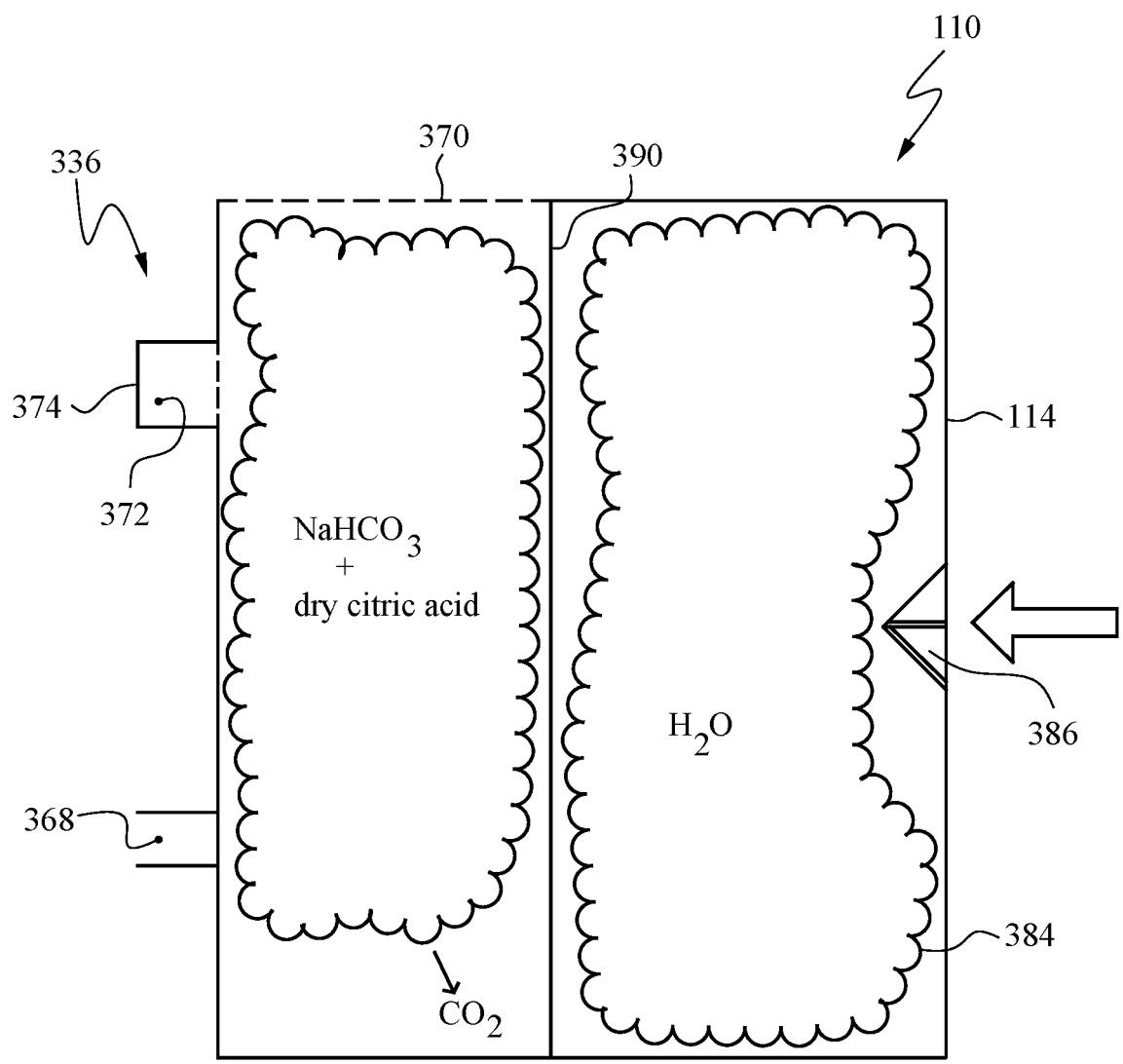
FIG. 10 is a cross-section side view of another workable fluid delivery system according to certain principles of the invention.
Figure 11:
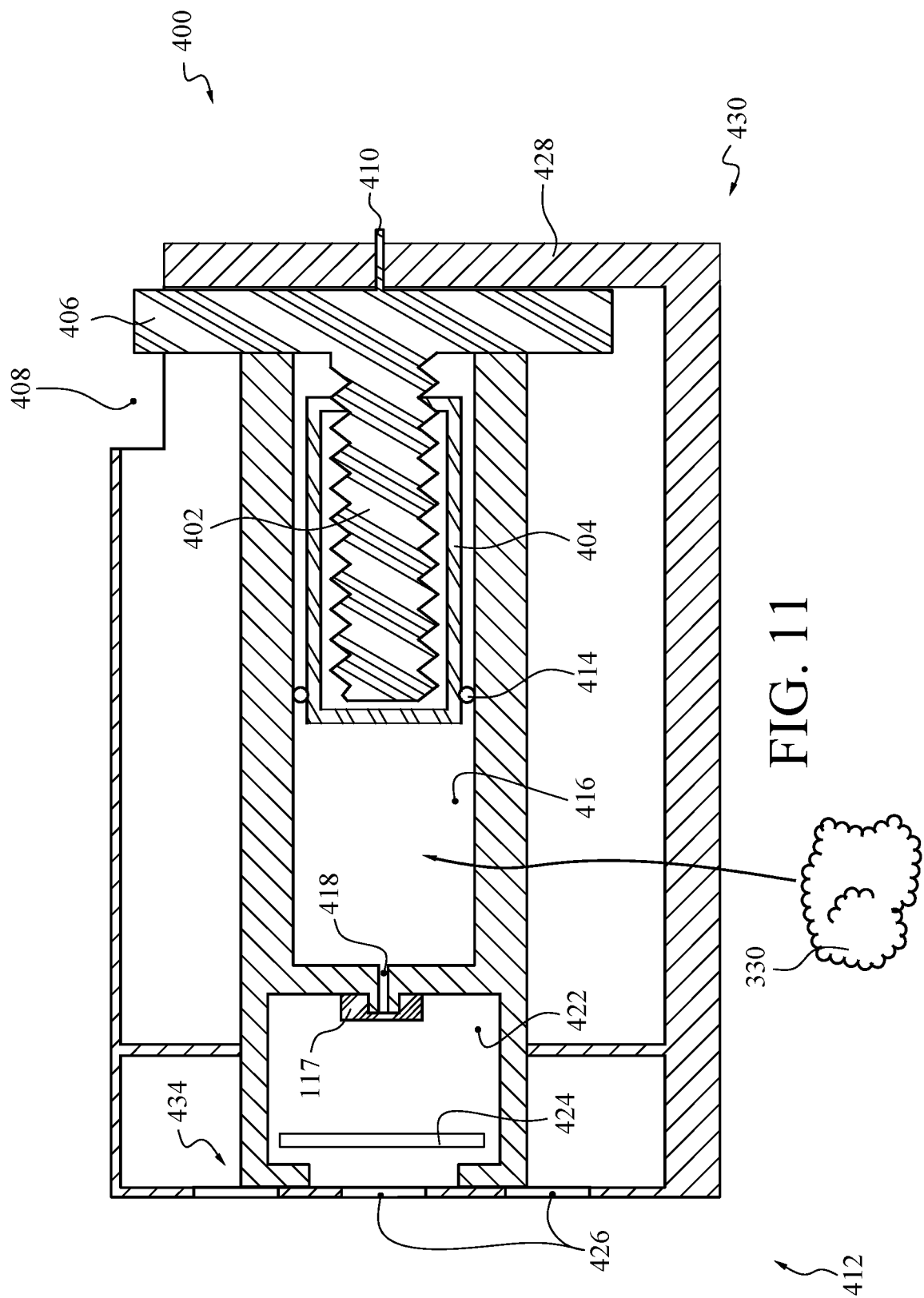
FIG. 11 is a schematic side view of another workable fluid delivery system according to certain principles of the invention.

In some delivery devices or pumps 100, the gas cell 110 is an electrochemical cell. Gas cell technology is taught by Gordon in U.S. Pat. Nos. 5,744,014 and 5,899,381 which are incorporated herein by reference The embodiment 100 illustrated in FIG. 1 includes a delivery aperture 112. In some embodiments, the delivery aperture 112 is a separate structure disposed in the delivery-side rigid portion 106. In other embodiments, the delivery aperture 112 is formed as part of the delivery-side rigid portion 106. The delivery aperture 112 allows a delivery material to be released from the delivery side 116 of the device 100. In some embodiments, a delivery aperture 112 may include a valve (e.g., 117 in FIG. 10) to prevent release of the delivery material until a certain pressure threshold or other criteria are reached. In some embodiments, the delivery aperture 112 includes an attachment point to facilitate attachment of a dispersion structure (discussed further below) to disperse the delivery material released through the delivery aperture 112. In some embodiments, the delivery aperture 112 is made of or includes an activator to cause a chemical reaction in the delivery material as it passes through the delivery aperture 112. For example, the delivery aperture 112 may include a heater, a chemical activator, an electrically charged element, or other structure to interact with the delivery material as it passes through the delivery aperture 112. In another embodiment, the delivery aperture 112 physically affects the delivery mode of the delivery material. For example, the delivery aperture 112 may atomize, collimate, stream, spread, accelerate, slow, vary, or modulate the delivery of the delivery material.

Although the delivery device 100 is shown and described with certain components and functionality, other embodiments of the delivery device 100 may include fewer or more components to implement less or more functionality.

Figure 2:
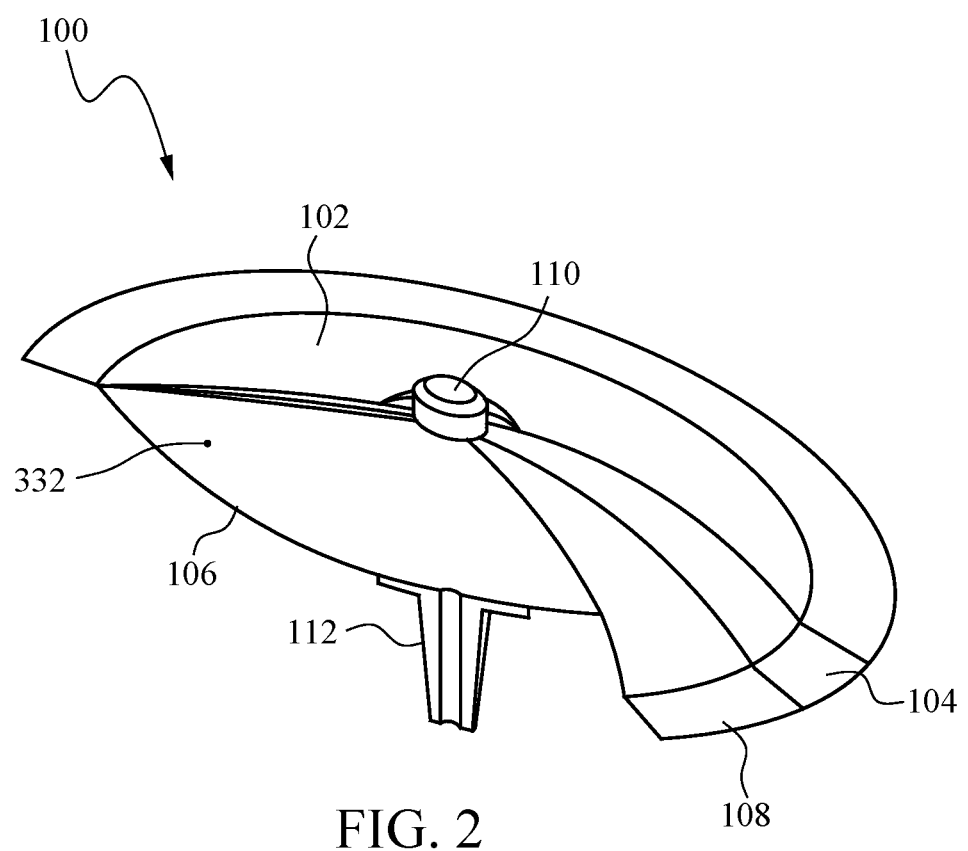
FIG. 2 depicts a cut-away schematic diagram in perspective of one embodiment of the delivery device of FIG. 1 with the gas-side flexible barrier fully compressed.

FIG. 2 depicts a cut-away schematic diagram of one embodiment of a delivery device 100 of FIG. 1 with the gas-side flexible barrier 104 fully compressed. The illustrated embodiment of the delivery device 100 includes the gas-side rigid portion 102, the gas-side flexible barrier 104, the delivery-side rigid portion 106, the delivery-side flexible barrier 108, the gas cell 110, and the delivery aperture 112.

As illustrated in FIG. 2, the delivery side (116, see FIG. 4) has been loaded with a delivery material so that the delivery-side flexible barrier is extended. This compresses the gas side (114, FIG. 4) so that the gas-side flexible barrier 104 conforms to the form of the gas-side rigid portion 102. Still with reference to FIG. 2, the gas cell 110 has not begun generating gas and the gas-side flexible barrier 104 is collapsed against the gas-side rigid portion 102. Once the gas cell 110 begins generating gas, the area between the gas-side rigid portion 102 and the gas-side flexible barrier 104 will fill with the gas and the gas-side flexible barrier 104 will begin to compress the delivery-side flexible barrier 108. This will result in increased pressure between the delivery-side flexible barrier 108 and the delivery-side rigid portion 106.

Figure 3:
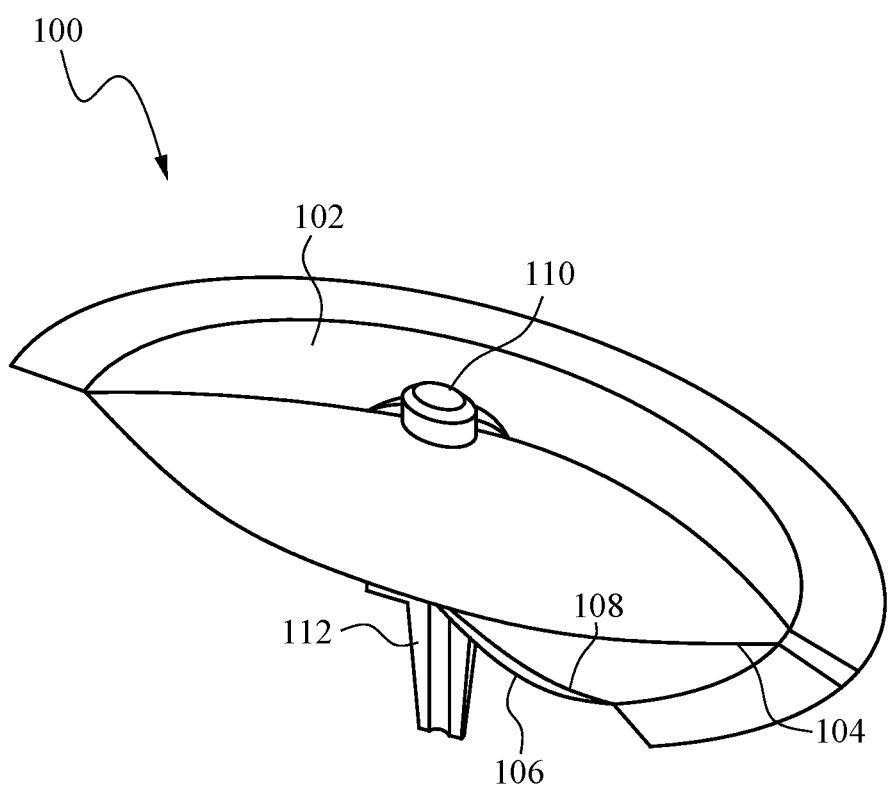
FIG. 3 depicts a cut-away schematic diagram in perspective of one embodiment of the delivery device 100 of FIG. 1 with the delivery-side flexible barrier fully compressed.

FIG. 3 depicts a cut-away schematic diagram of one embodiment of the delivery device 100 of FIG. 1 with the delivery-side flexible barrier 108 fully compressed. In the illustrated embodiment, the gas cell 110 has generated enough gas to force the gas-side flexible barrier 104 away from the gas-side rigid portion 102 to compress the delivery-side flexible barrier 108. This has expelled the delivery material through the delivery aperture 112 and collapsed the delivery-side flexible barrier 108 against the delivery-side rigid portion 106.

Figure 4:
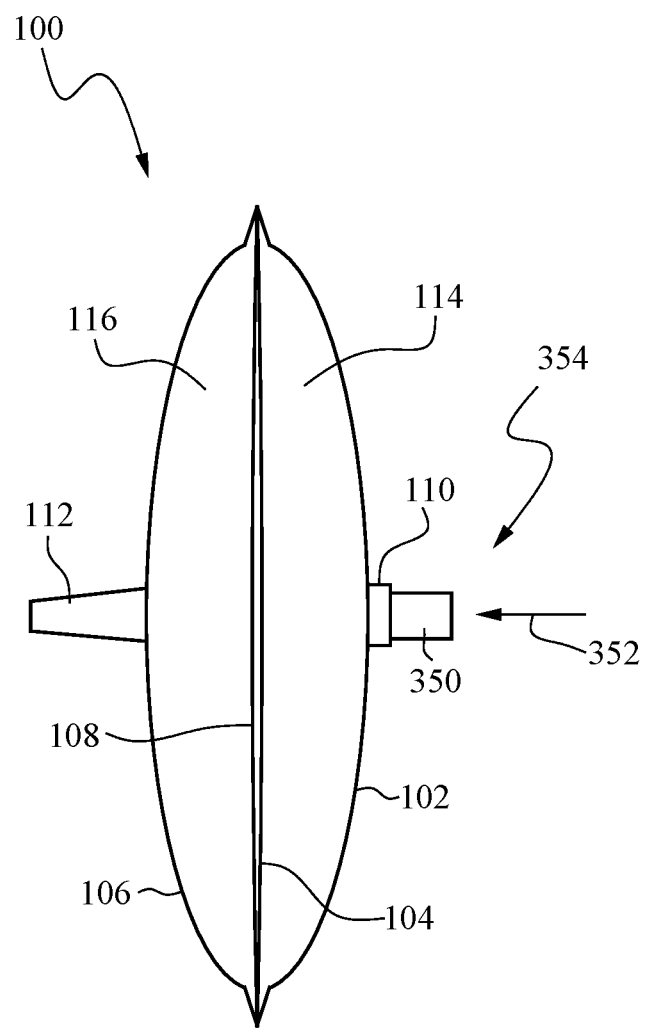
FIG. 4 depicts a schematic diagram side view of one embodiment of the delivery device of FIG. 1 with the flexible barriers and in neutral position, and a gas generating cell in storage-stable configuration.

FIG. 4 depicts a schematic diagram of one embodiment of the delivery device 100 of FIG. 1 with the flexible barriers 104 and 108 in neutral position. In the illustrated embodiment, the gas-side flexible barrier 104 and the delivery-side flexible barrier 108 are in neutral position. This more readily depicts the gas chamber 114 or gas side 114 of the delivery device 100 as well as the delivery chamber 116 or delivery side 116 of the delivery device 100. In the illustrated embodiment of FIG. 4, the gas-side flexible barrier 104 and the delivery-side flexible barrier 108 are separated by a small margin. In some embodiments, the relatively small space between the gas-side flexible barrier 104 and the delivery-side flexible barrier 108 is filled with a buffer material to reduce friction and binding between the gas-side flexible barrier 104 and the delivery-side flexible barrier 108. In other embodiments, the gas-side flexible barrier 104 and the delivery-side flexible barrier 108 are in direct contact without separation. In some embodiments, one or both of the gas-side flexible barrier 104 and the delivery-side flexible barrier 108 include surface treatments to reduce friction and substantially prevent binding between the gas-side flexible barrier 104 and the delivery-side flexible barrier 108.

Figure 6:
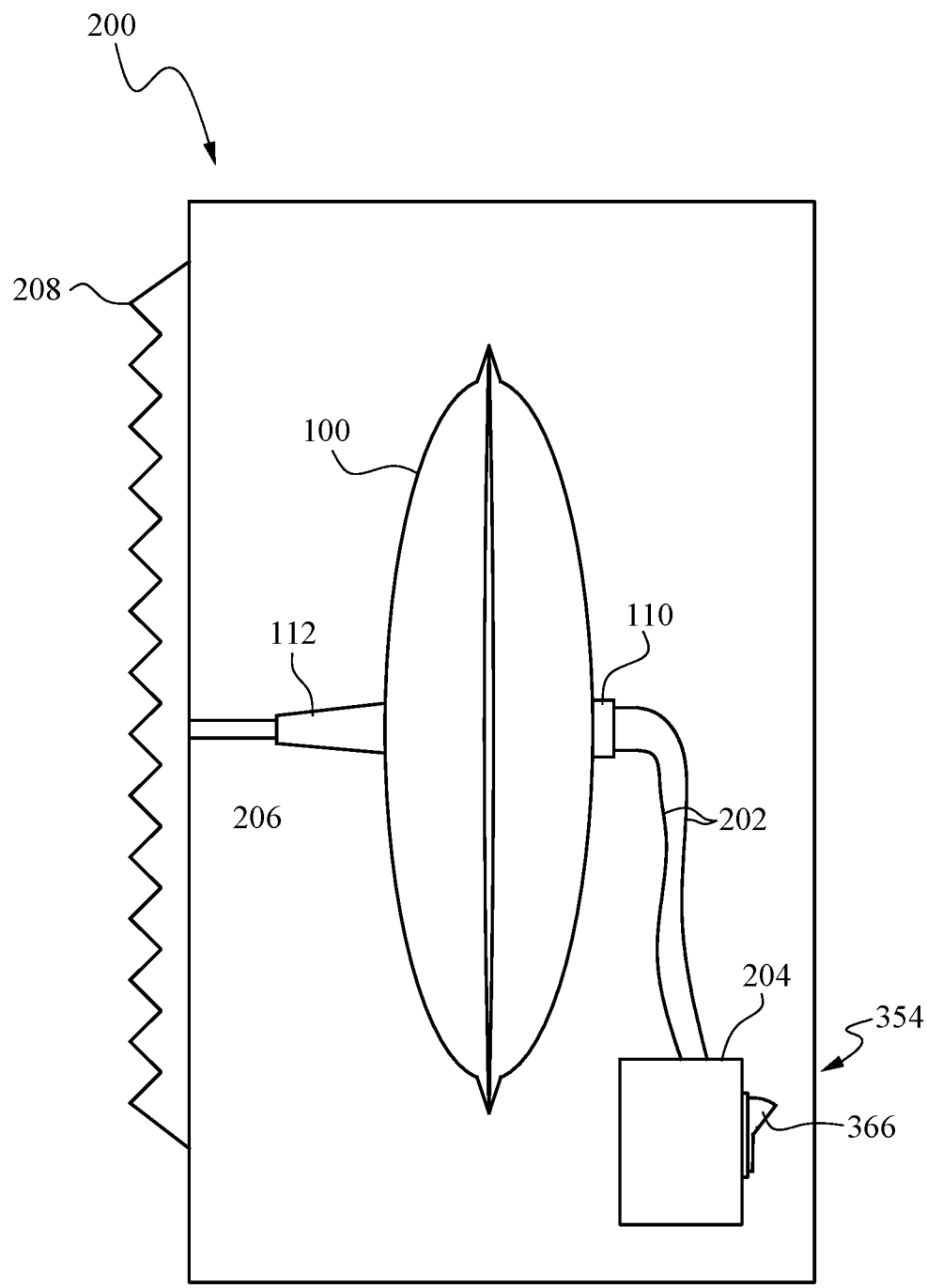
FIG. 6 depicts a schematic diagram side view of one embodiment of the delivery device of FIG. 1 with the flexible barriers and in neutral position, and a remote gas generating cell.

FIG. 6 depicts a schematic diagram side view of one embodiment of a delivery system 200. The illustrated embodiment 200 includes a delivery pump 100, a control module 204, leads 202, delivery line 206, and dispersion structure 208. In the illustrated embodiment, the pump 100 includes a gas cell 110 and a delivery aperture 112. In the illustrated embodiment, the pump 100 is in a vertical orientation. In other embodiments, the pump may be oriented horizontally, or at some other angle. In the illustrated embodiment, the gas cell 110 is connected by leads 202 to a control module 204. In some embodiments, the control module 204 includes resistive elements to control the gas cell 110. Other embodiments include other types of electrical or mechanical control systems.

In the illustrated embodiment 200, the delivery aperture 112 is connected to the delivery line 206. In some embodiments, the delivery line 206 is a tube or channel. The delivery line 206 is connected to the dispersion structure 208 to communicate a delivery material from the delivery aperture 112 of the pump 100 to the dispersion structure 208. In some embodiments, the delivery line 206 is omitted and the delivery aperture 112 is in direct communication with the dispersion structure 208. In some embodiments, the dispersion structure 208 is a molecular dispersion media. For example, the dispersion structure 208 may include gauze, foam, sponge, or other breathable surface area. In another embodiment, the dispersion structure 208 is a spray nozzle. In other embodiments, the dispersion structure 208 is a tube, a needle, a heated element, or other known mechanical, thermal, chemical or other element for delivery of a material to a target location or environment. In another embodiment, the dispersion structure 208 is omitted and the delivery aperture 112 disperses the delivery material from the pump directly out from the delivery system 200. In some embodiments, the pump 100 is implemented within the delivery system 200 to provide certain advantages over conventional technologies. For example, some embodiments of the delivery system 200 implement the pump 100 to eliminate orientation dependencies. For example, the delivery system 200 may be oriented in any direction without suffering leakage or failure in the pump 100. Other embodiments of the delivery system 200 may implement the pump 100 to achieve other advantages.

Although the delivery system 200 is shown and described with certain components and functionality, other embodiments of the delivery system 200 may include fewer or more components to implement less or more functionality.

Figure 7:
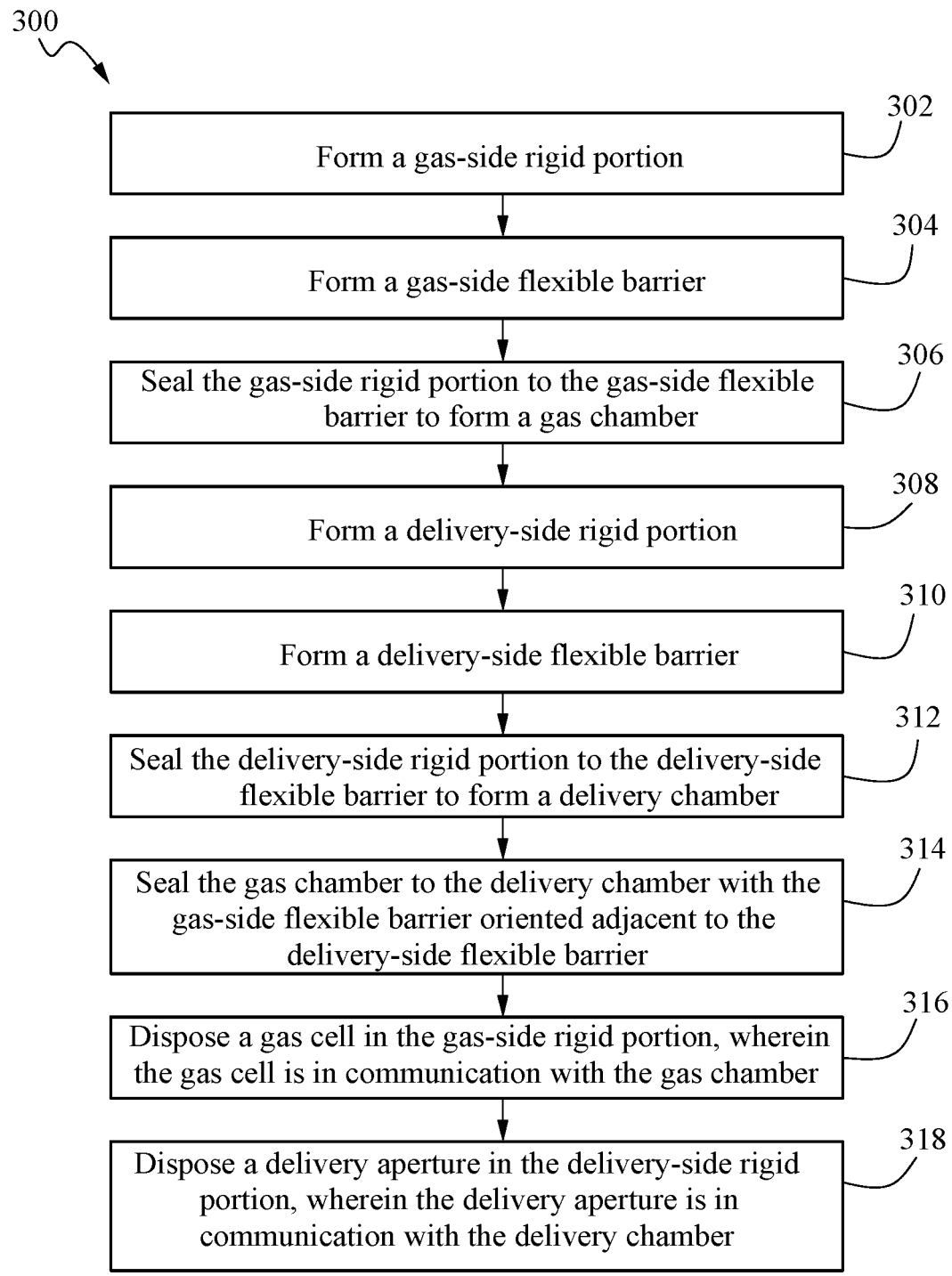
FIG. 7 depicts a block diagram of one embodiment of a method of manufacturing a multi-chamber delivery system.
Figure 8:
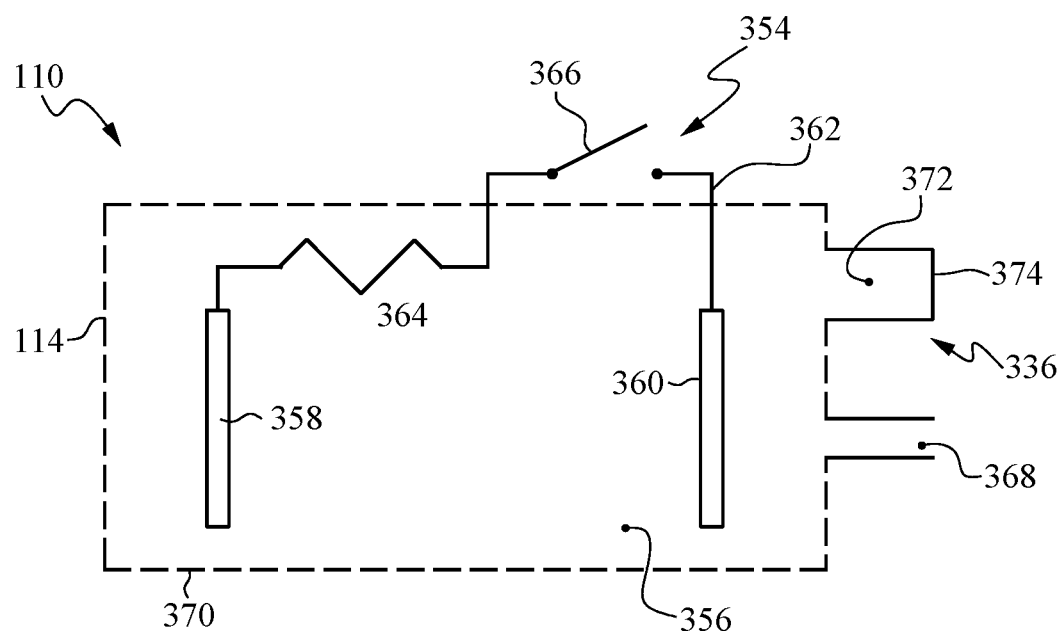
FIG. 8 is a schematic view of gas generating cell operable for use in a fluid delivery system according to certain principles of the invention.
Figure 9:
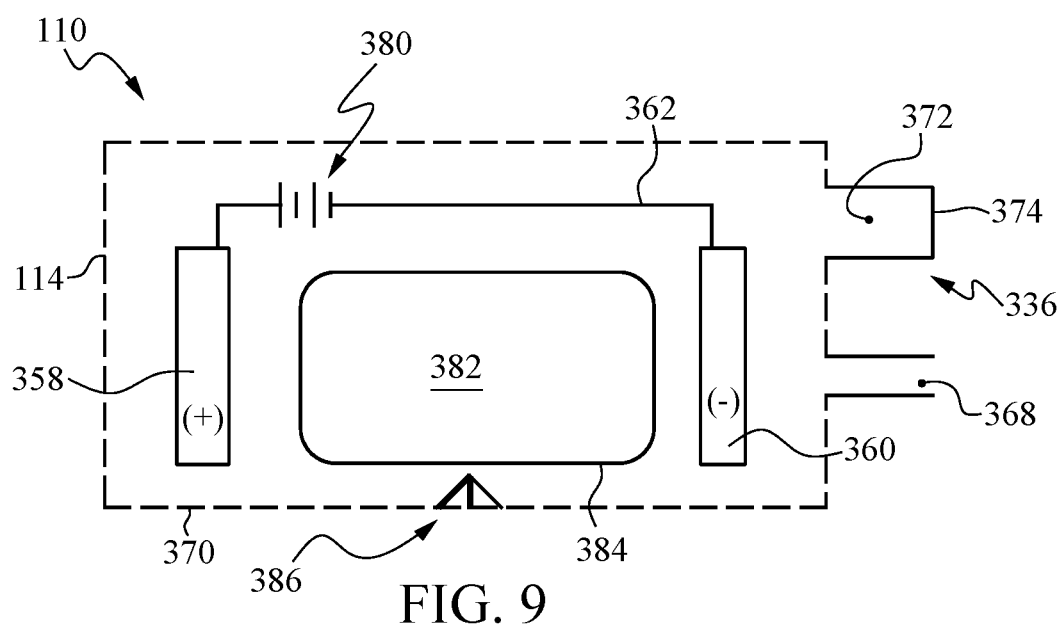
FIG. 9 is a schematic view of a gas generating cell operable for use in another workable fluid delivery system according to certain principles of the invention.

FIG. 7 depicts a block diagram of one embodiment of a method 300 of manufacturing a chamber delivery system. At block 302, a gas-side rigid portion is formed. At block 304, a gas-side flexible barrier is formed. At block 306, the gas-side rigid portion is sealed to the gas-side flexible barrier to form a gas chamber. At block 308, a delivery-side rigid portion is formed. At block 310, a delivery-side flexible barrier is formed. At block 312, the delivery-side rigid portion is sealed to the delivery-side flexible barrier to form a delivery chamber. At block 314, the gas chamber is sealed to the delivery chamber with the gas-side flexible barrier oriented adjacent to the delivery-side flexible barrier. At block 316, a gas cell is disposed in the gas-side rigid portion. The gas cell is in communication with the gas chamber. At block 318, a delivery aperture is disposed in the delivery-side rigid portion. The delivery aperture is in communication with the delivery chamber.

It is desirable to provide structure or to otherwise craft a device 100 to resist spill of delivery material from the device 100. Gas that is present in the delivery chamber 116 and that undergoes a temperature increase may cause a much larger undesired discharge of delivery material than expansion of the storage material, itself, due to the same temperature increase. Therefore, it is desirable to minimize gas entrapped inside the storage chamber 116. With reference again to FIG. 1, it is within contemplation to include an absorbent element 330, such as a sponge, to facilitate completely filling the storage volume 332 of a delivery chamber 116 with delivery material during manufacture of a device 100. In that case, entrapment of air bubbles in the storage/delivery chamber 116 when charging the chamber 116 with a delivery material is significantly reduced, or desirably, eliminated. The resulting device 100 is more resistant to spilling or undesirably discharging delivery material 334 due to an increase in temperature of the storage or service environment. A preferred absorbent element 330 is configured to virtually or completely fill the volume of a fully charged delivery chamber 116 when saturated or loaded with the delivery material.

Sometimes, a gas generating cell 110 may generate a spurious small amount of gas during storage or other non-operating periods. For purpose of this disclosure, such spurious gas is characterized as passive gas, or non-operating gas. Non-operating gas generation may occur at a Zinc electrode when that electrode is bathed in an electrolyte, due to impurities that are realistically inherent in that electrode, for one example. Also, an electrolyte may contain a certain amount of reactive ions that react at an electrode to generate gas until a protective surface film is developed on the electrode, for a second non-limiting example. Therefore, as an alternative or additional measure to reduce spilling or undesired discharge of delivery material from confinement in the delivery chamber 116 to the environment, a passive gas-relief valve 336 may be included in a venting association with a gas chamber 114. As illustrated in FIG. 1, a workable passive gas-relief valve 336 may be structured as a gas-permeable membrane disposed to cover a window through gas-side rigid portion 102. A gas-relief valve 336 is operable to permit a certain small amount of gas (e.g., passive gas) to slowly migrate from chamber 114 through the valve 336 to the environment to avoid pressure build-up inside the gas chamber 114. Therefore, the small quantities of gas, which may be slowly generated by a gas generating cell 110 during non-operational storage of a device 100, will not accumulate and create a discharge pressure to cause a spill of delivery material. However, a workable gas-relief valve 336 does not permit gas discharge from chamber 114 at a rate sufficient to reduce operational capability of the device 100 once the gas generating cell 110 is placed into an operation mode to generate gas for conventional use of device 100.

As another option to reduce or avoid spills of delivery material, an overflow emanator chamber 338 may be associated with a delivery aperture 112 to receive small quantities or even excessive drops of delivery material 334. Desirably, an overflow emanator chamber 338 is structured to confine a volume 340 that is at least about half the volume of delivery material that is initially confined in delivery chamber 116. As another option, it is within contemplation to further include an absorbent element 342 disposed inside the volume 340. In the latter case, undesirably discharged drops of delivery material 334 may be captured and confined to resist spilling delivery material from the device 100. A workable absorbent element 342 may be a sponge, or other such material that can soak up delivery material, and permit emanation of desirable volatile portions thereof. Desirably, absorbent element 342 is also effective as an emanator, or serves to communicate absorbed delivery material to an emanator.

Figure 5:
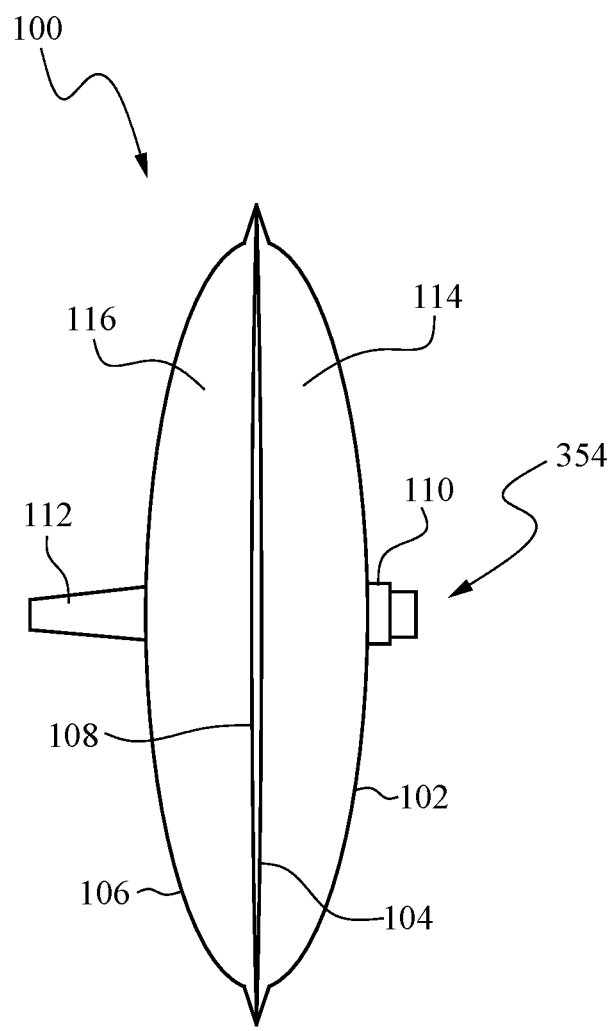
FIG. 5 depicts a schematic diagram side view of the embodiment in FIG. 4 with a gas generating cell in an operational configuration.

It is within contemplation that a gas generating valve 110 may be structured to resist generation of gas prior to placing the valve 110 into operation to dispense delivery material. With reference to FIGS. 4 and 5, a gas-generating valve 110 may be structured for storage in a configuration that decouples at least one reactive element from operational contact with another element. In FIG. 4, the valve 110 is illustrated in a decoupled configuration. Displacement of element 350 in an actuating direction (such as transverse direction 352) to couple elements or otherwise permit operation of valve 110 is effective to enable the gas-generating valve 110 to produce gas, as illustrated in FIG. 5. An actuation direction may be embodied to include one or more of a displacement and a rotation.

Operable de-coupling structure, generally indicated at 354, may be configured, as non-limiting examples, to interrupt an electric path between electrodes, or to isolate an electrolyte from operational contact with electrodes. A portion of a gas-generating cell 110 may even be provided as an element that is physically separate from the bulk of a device 100, and the distinct elements can be coupled together in an operational configuration to generate operational quantities of gas at the time the device 100 is placed into service to dispense delivery material. In the latter case, decoupling structure encompasses distance and physical separation between constituent elements. Discrete elements within contemplation include individual active elements, such as electrolyte, or a portion of a conductive path extending between electrodes of the cell. The gas generating cell, itself, can even be stored as a discrete component and assembled in operational registration with a gas chamber at the time when a device 100 is placed into service.

FIG. 8 illustrates a self-powered galvanic gas cell 100 that is structured to resist an internal build-up of passive gas. The gas chamber 114 holds an electrolyte 356 in operable association with a Zinc anode 358 and carbon cathode 360. A workable electrolyte includes KOH and $H_2O$. An interruptible electrically conductive path 362 (e.g., a metal wire) is provided between the anode and cathode. Hydrogen gas $H_2$ is evolved at the Zinc anode 358, according to the overall reaction $Zn+H_2O \Rightarrow ZnO+H_2$, and the rate of gas production can be controlled by the value of the resistor 364. A workable resistor may have a resistance between about 1000 and about 8000 ohms. It is preferred to include decoupling structure 354, such as switch 366 to place the cell 110 in either an operational condition, or a non-operational condition, as desired. Evolved operational gas may be ported through exit 368 to a different remote gas chamber (not illustrated), or a wall 370 of chamber 114 may be embodied as a flexible membrane to engage a cooperating membrane of a proximal delivery chamber 116. An optional passive gas-relief valve 336 may be included. Illustrated gas-relief valve 336 includes a window 372 through a wall of the chamber 114, and a gas permeable membrane 374 to allow escape of passive gas, while resisting undue escape of operational gas.

FIG. 9 illustrates an electrochemical gas generating cell 110 that is also structured to resist an internal build-up of passive gas. Certain elements are similar to like elements in FIG. 8, and are numbered accordingly. An external power source, generally 380, is operably connected to anode 358 and cathode 360 by way of conductor 362. Initially, a quantity of electrolyte 382 is confined inside membrane pouch 384, and is therefore prevented from reacting with the anode and cathode. As illustrated, a puncture device, generally 386, may be arranged to puncture the membrane 384 and thereby permit electrolyte 382 to react with the anode and cathode under influence of, and generate a gas when the cell 110 is placed into operational mode.

FIG. 10 illustrates another gas cell 110 that is structured to resist build-up of passive gas during storage of a delivery device 100. Again, certain elements are similar to like elements in FIGS. 8 and 9, and are numbered accordingly. A quantity of sodium carbonate and anhydrous citric acid are disposed on one side of a moisture-permeable membrane 390 inside gas chamber 114. A fluid, such as water ($H_2O$) is disposed on the other side of membrane 390, and is initially confined in a membrane pouch 384. When the gas cell is to be used to generate gas, puncture device 386 may be used to release the fluid from confinement. In the case where the fluid is water, the water can pass through the membrane 390 to react with the sodium carbonate and anhydrous citric acid. The reaction rate and corresponding evolution of gas ($CO_2$) will be at a rate controlled by permeation properties of the membrane 390. Passive gas is not evolved in the embodiment illustrated in FIG. 10, because dry sodium carbonate and anhydrous citric acid do not react without the presence of fluid. However, a passive gas relief valve 336 may be included to accommodate a pressure change during storage, where the pressure change corresponds to temperature change in air unavoidably present in chamber 114.

FIG. 11 illustrates another embodiment of a manual fragrance delivery system 400 which includes a threaded actuator shaft 402 that is rotated by way of a user interacting with actuator knob 406. Threaded shaft 402 engages a threaded wall at the proximal end of the piston plunger 404. Window 408 provides access for a user's finger to engage actuator knob 406. Knob 406 may be rotated about axle 410 to cause a compression in the shaft 402 and drive piston plunger 404 toward the discharge end, generally indicated at 412. Piston plunger 404 is sealed on its distal end, as indicated at O-ring 414, to urge volatile fluid contained inside plunger chamber 416 (AKA volatile fluid or delivery material chamber 116) toward aperture 418 for discharge into the local environment.

Certain embodiments may include a valve member 117 to resist unintended discharge of fluid. One operable valve member 117 establishes a threshold pressure required before fluid is permitted to flow through the discharge aperture 418.

Further, a safety emanator chamber 422 may be provided to hold a quantity of fluid that is improperly, or accidentally, discharged. For example, a child may play with the discharge mechanism 406 and discharge a significant portion of fluid. Safety reservoir 422 provides a catch basin to hold the fluid, rather than permit the fluid to leak onto and damage e.g., upholstery or carpeting in an automobile. A safety reservoir 422 within contemplation may be sized to hold the entire initial (or as-manufactured) contents of volatile fluid chamber 416. Preferably, emanator chamber 422 is sized to accommodate at least half the volume that is confined in chamber 416 at time of manufacture. An emanator 424 is typically provided to facilitate distribution and evaporation of the volatile fluid in chamber 422 over a larger area. Evaporated volatile fluid is then dispensed to the local environment through one or more apertures 426.

It is preferred for threaded shaft 402 to be left-hand threaded. As indicated above, the threaded shaft 402 is placed into compression to urge motion of plunger 404. The proximal end portion 428 of housing 430 forms a fixed restraint against which the actuator knob 406 presses to urge motion of the plunger 404. The window 408 is formed in housing 430, and permits a user access to manipulate actuator knob 406. Foot 434 is engaged on discharge end 412, so as plunger 404 moves distally, a volume in chamber 416 can be reduced to discharge volatile fluid from the chamber 416. As is the case with certain other embodiments, sometimes an absorbent element 330 may be included in the delivery chamber 416 to facilitate removal of gasses from the chamber 416 during manufacture of a device 400. The absorbent element 330 collapses, as the volume of chamber 416 is reduced by displacement of plunger 404, to release volatile fluid for discharge through aperture 418 toward a local ambient environment. It is further within contemplation that an absorbent element 330 may also, or alternatively, be disposed inside safety emanator reservoir 422, similar to a previously described embodiment.

Figure 12:
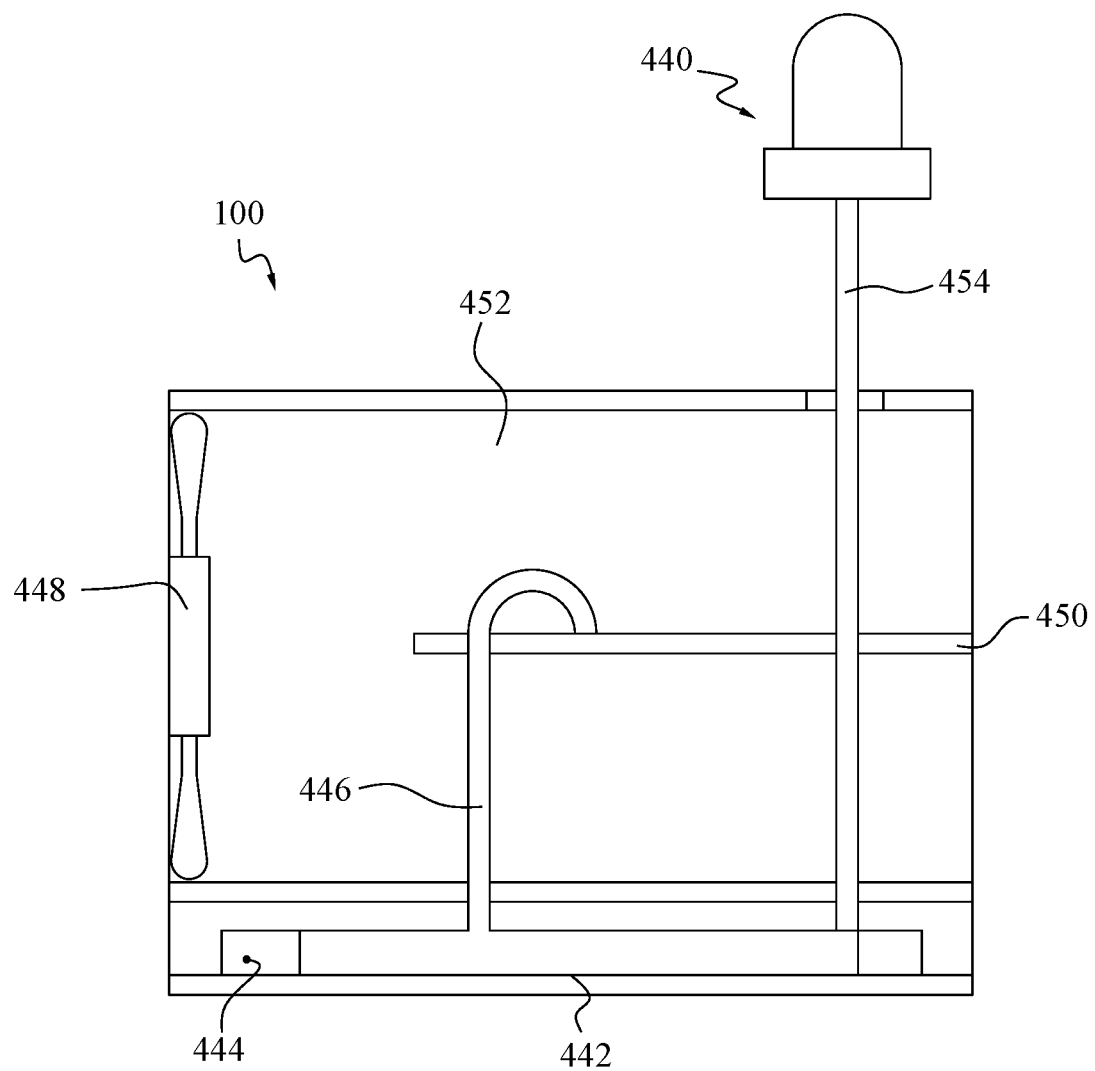
FIG. 12 is an alternative embodiment of a pressurized chamber fragrance delivery system.

FIG. 12 illustrates an alternative embodiment of a pressurized chamber fragrance delivery system 100 configured to impart fragrance to a local environment. The illustrated pressurized chamber fragrance delivery system 100 includes a manual pump 440, a fragrance bag 442, an air chamber 452, a fragrance exit channel 446, a fan 448, an emanator 450, an air channel 452, and an air tube 454. Although the illustrated pressurized chamber fragrance delivery system 100 includes certain components to achieve specific functionality, other embodiments of the pressurized chamber fragrance delivery system 100 may include fewer or more components to achieve similar or different functionality.

In one embodiment, the manual pump 440 is used to pressurize the air chamber 444 containing the flexible fragrance bag 442. In one embodiment, the manual pump 440 is a manual air pump. Other embodiments may use other types of pumps. Pressurizing the air chamber 444 compresses the fragrance bag 442 to expel fragrance from the fragrance bag 442 through the fragrance exit channel 446 to the emanator 450. Some examples of emanator materials include, but are not limited to, porous polymers, simple cellular papers or films. In general, embodiments of the emanator 450 have a balance of absorption, wicking, and emanation properties that allow the emanator 450 to collect, distribute, and release the fragrance over time. The fan 448 moves air over the emanator 450 to deliver the fragrance into the ambient environment.

In some embodiments, the emanator 450 includes a porous material to collect, wick, and release the fragrance. The emanator 450 may or may not have its own structural integrity to maintain a specific shape while mounted within the fragrance delivery system. In some embodiments, the emanator material is applied to, or supported by, another support structure such as a cage or frame made of any suitable material.

Figure 13:
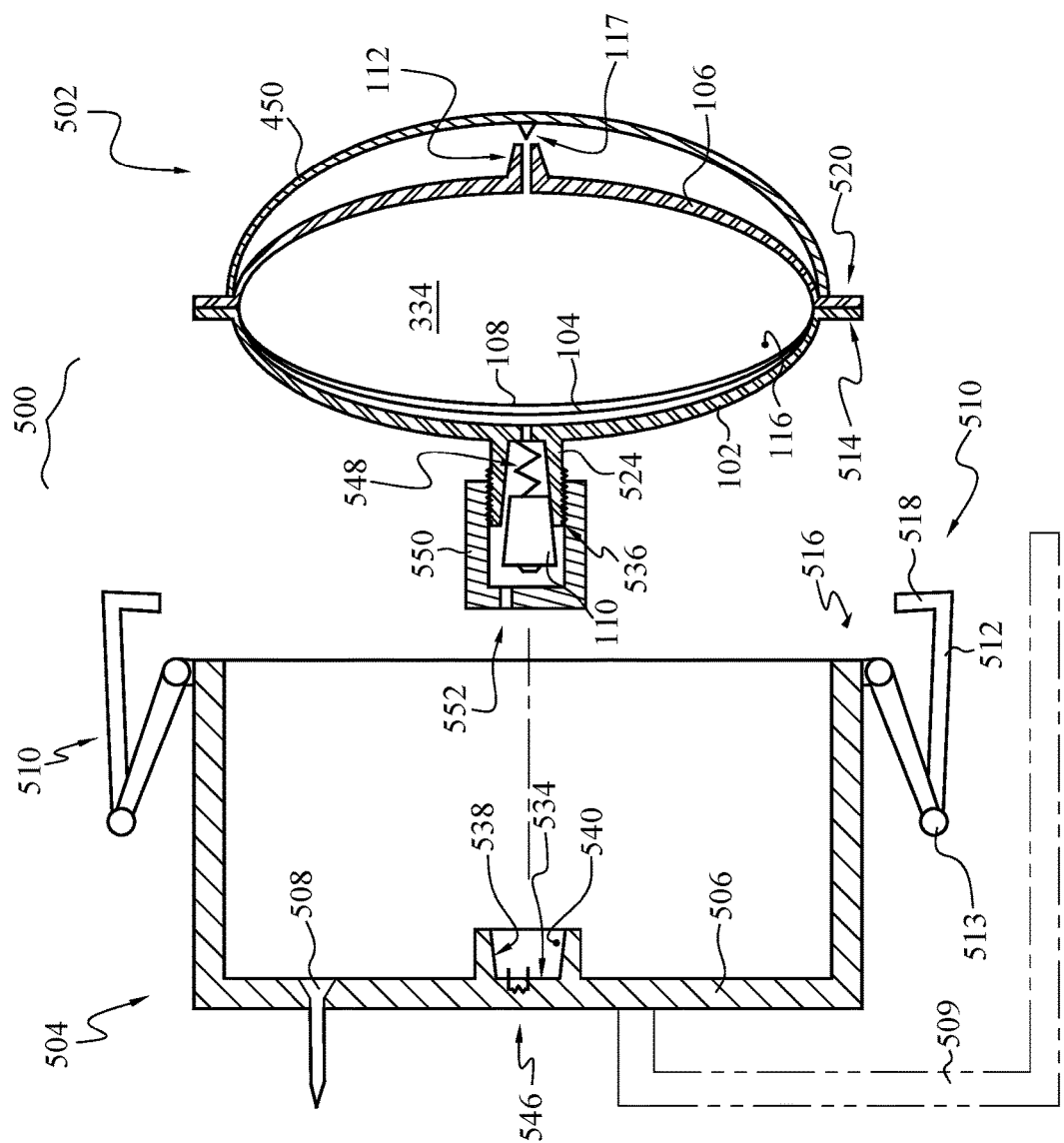
FIG. 13 is a schematic side view in cross-section of another embodiment taken through a central plane.

With reference to FIG. 13, an embodiment generally indicated at 500 includes a replaceable cartridge 502 and a cooperating foundation 504 on which to support the cartridge 502. A workable cartridge 502 may be similar to embodiment 100 illustrated in FIGS. 1-6, and may optionally include components, or elements, illustrated in any other of the above-described embodiments. Some of the illustrated elements may be redacted, and/or other elements disclosed in this document may be added to form alternative workable embodiments 500.

A foundation 504 may have a base 506 structured to be attached in some way to a substantially vertical surface, such as a wall, and as indicated by mounting screw 508. Illustrated base 506 may be characterized as a hollow cup in which a portion of cartridge 502 is carried and can be installed in substantially permanent registration with a wall. In a different arrangement, a foundation 504 may be structured for free-standing support on a table, toilet tank cover, vanity top, floor, or other substantially horizontal surface. For example, an optional foot 509 (illustrated in phantom line) may be provided in certain embodiments.

Desirably, a retention mechanism, generally indicated at 510, is provided to facilitate holding a cartridge 502 in conveniently releasable assembled registration with a foundation 504. In FIG. 13, retention mechanism 510 includes a plurality of toggling clamp mechanisms 512. Clamp mechanisms 512 are illustrated in an arbitrary intermediately-rotated position. In use of a clamp 512, a rear surface 514 of cartridge 502 is held against distal surface 516 of base 506, and the clamp foot 518 presses onto front surface 520. Typically, hinge 513 toggles toward contact with the sidewall of base 506 to generate a clamping force and hold a cartridge 502 in registration with base 506. A clamp 512 may be structured to permit tool-free release of a spent cartridge 502.

Figure 14:
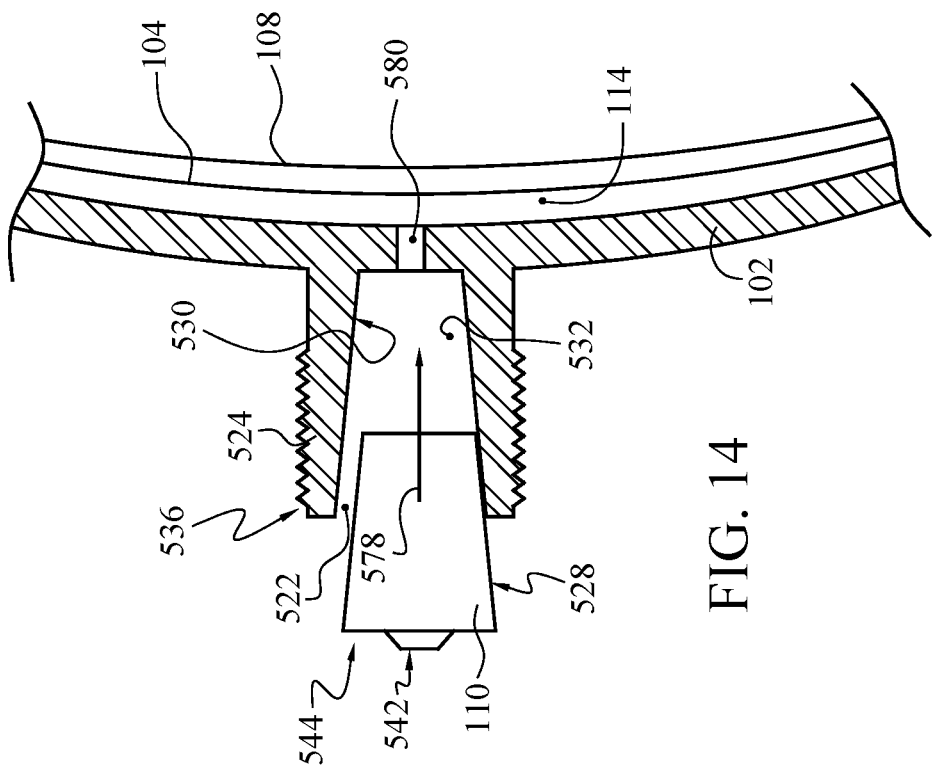
FIG. 14 is a close-up view of a gas-generating cell portion of the embodiment in FIG. 13.

With reference to FIGS. 13 and 14, certain embodiments may provide a leak path for passive gasses. Sometimes, passive gas is generated prior to assembly of a cartridge 502 and foundation 504. Other times passive gas may be generated subsequent to assembly. The primary function of a leak path for passive gas is to prevent undesired build-up of fluid pressure inside the delivery chamber 116 while a device is being stored prior to use as a fluid dispenser. The built-up pressure from passive gas can cause undesired discharge of fluid (leaking) from the cartridge 502.

One leak path for passive gas within contemplation includes vent path 522 disposed between a gas cell 110 and cell-holding structure, generally indicated at 524, of a gas-side rigid portion 102. Vent path 522 is closed or occluded upon placing the cartridge 502 in seated engagement with base 504. As illustrated, gas cell 110 can be structured to have a perimeter seal surface 528 that seals against cooperating inside surface 530 of socket 532 when the cartridge 502 is installed in a base 506. Structure associated with floor 530 can be configured to press gas cell 110 into such a sealed position upon installation of cartridge 502 and base 506. Alternatively (or in addition), cone end surface 536 may be configured to seal in cooperation with inside surface 538 of socket 540 upon assembly of a cartridge 502 and foundation 504.

It should be noted that the gas generating cell 110 of assembly 500 in FIG. 13 is only placed into active gas-generation mode upon assembly of a cartridge 502 to a base 504. In the installed position, an electrical circuit is established between the anode 542 and the cathode 544 (see also FIG. 14). The base 504 carries electronics, generally 546, that complete an external electrical path between anode 542 and cathode 544 upon assembly of the base and cartridge components. Electronics 546 typically encompass a resistor, e.g., in the case where gas cell 110 generates Hydrogen gas. In that case, the resistor may be sized to cause a desired rate of gas generation for a specific application. It is within contemplation that electronics 546 may encompass one or more resistor, battery, switch, and/or other electrical circuit element.

With further reference to FIGS. 13 and 14, a gas cell 110 may be carried in loose association with a cell-holding structure 524. A gas cell 110 may be maintained in a spaced-apart relation to a cooperating seal surface 530 by keeper structure such as a compression spring element, generally 548. Spring 548 may maintain the cell 110 in a loose but attached relationship to a cartridge 502. Force generated by spring 548 inherently resists undesired occlusion of vent path 522, but may be overcome upon assembly of cartridge 502 to a base 504 by a user at the time when a device is placed into service to dispense fluid.

It is within contemplation to provide alternative keeper structure, such as a removable threaded cap 550, which is removed by a consumer prior to assembly of the assembly 500. Sometimes, a gas vent 552 may be provided in a cap 550. Alternative devices to hold a gas cell in venting association with a cartridge 502 are within the skill of an artesian. As one non-limiting example, a consumer-removable piece of tape may be applied to hold the cell 110 in a venting position with respect to the cartridge 502.

Figure 15:
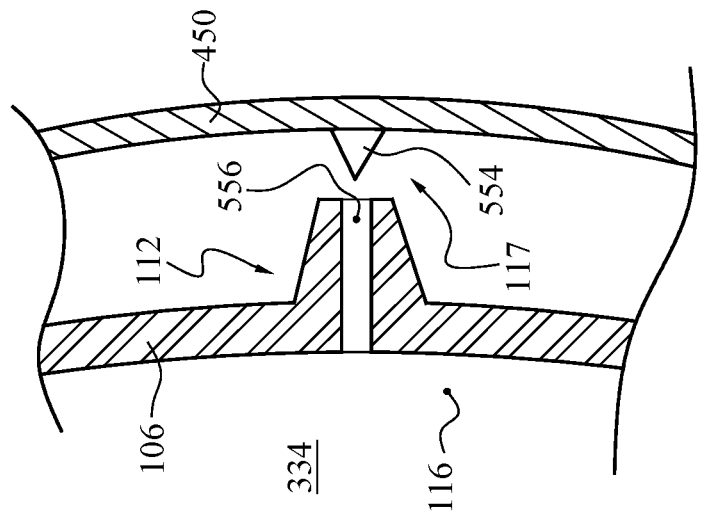
FIG. 15 is a close-up view of a fluid discharge portion of the embodiment in FIG. 13.

It is sometimes desirable to provide a threshold pressure valve 117 to resist undesired escape of fluid 334 from delivery chamber 116. For example, fluid 334 or bubbles entrained in fluid 334 may expand due to a temperature change, and valve 117 may resist fluid escape in that circumstance. Valve 117 may also be configured to resist escape of fluid delivery material 334 by way of capillary draw-out by and/or to an emanator 450. As shown in FIGS. 13 and 15, a workable threshold pressure valve 117 may be formed by a biased stopper 554 that engages and normally-occludes orifice 556 in fluid delivery aperture 112. (Note the elements of valve 117 are illustrated in a non-operational spaced-apart relationship for clarity of disclosure). Sufficient pressure on fluid 334 (e.g., generated by an energized, activated, or operating gas cell 110), is then operable to displace the stopper 554 and burp out a quantity of fluid 334 for absorption by, and distribution over, emanator 450 and subsequent evaporation into the local environment. A workable stopper 554 may be carried by an emanator, such as illustrated emanator 450 in FIG. 15. Alternatively, a stopper 554 may be carried by a self-biasing element separate from an emanator 450.

Figure 16:
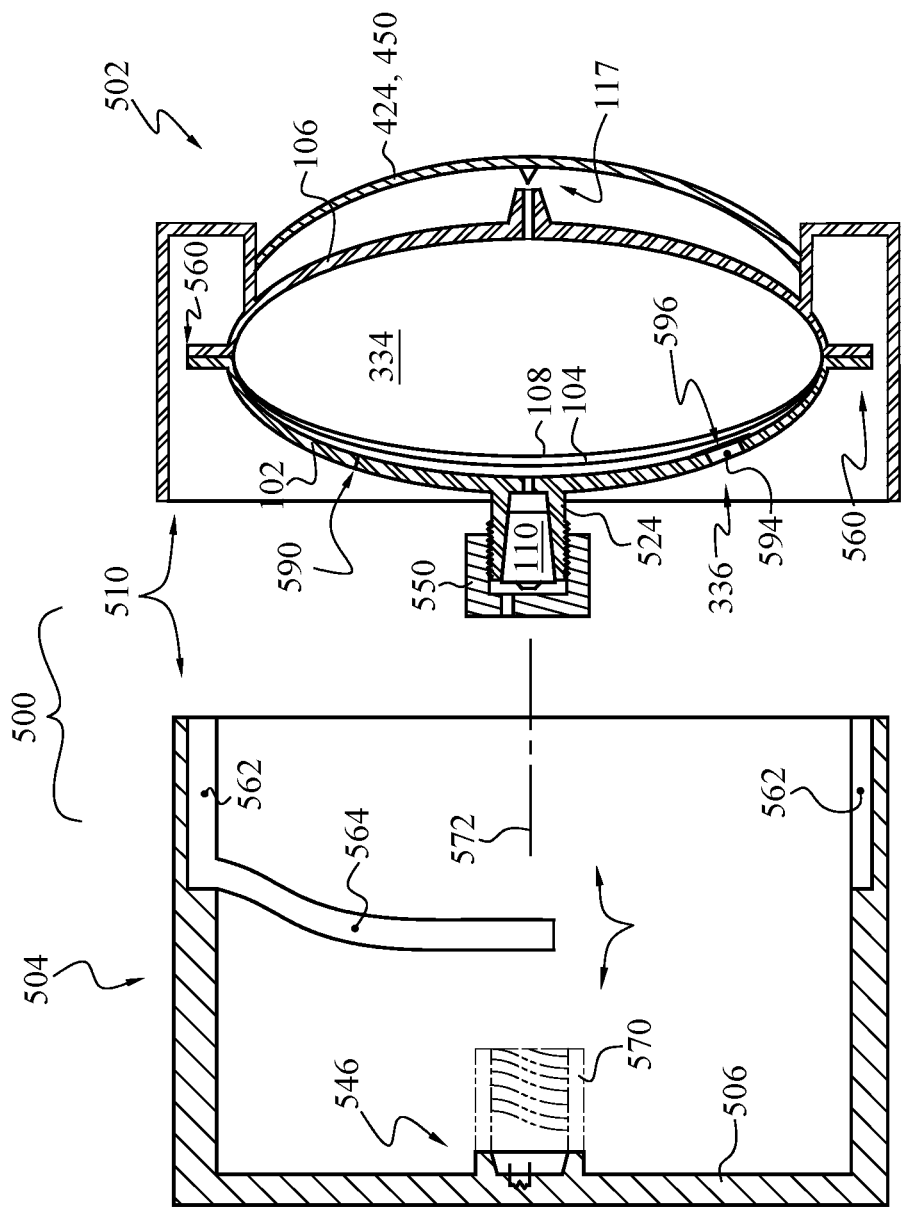
FIG. 16 is a schematic side-view in cross section of another embodiment taken through a central plane.

The embodiment 500 illustrated in FIG. 16 also includes a foundation 504 that may hold one of a selected replaceable cartridge 502. FIG. 16 illustrates several elements that may be present in an embodiment, but may not all be present together in a single embodiment. One retention mechanism 510 includes a tang or partial thread generally indicated at 560. Tangs 560 are received for axial reciprocation in slots 562 as the cartridge 502 is partially seated in foundation 504. Tangs 560 then follow a path defined by grooves 564 as the cartridge 502 is rotated with respect to the foundations 504. The lead present in the grooves 564 cause the cartridge 502 to be snugged up in registration with the base 506, at which point the cell 110 is seated in operable registration with electronics 546, and may also seat the cell 110 in sealing registration with respect to the rigid element 524.

An alternative illustrated retention mechanism 510 may include male threads on element 524 that are exposed after a consumer removes a removable cap 550 in preparation for assembling a device 500. Such male threads may be received in an extension socket 570 that carries cooperating female threads. Rotation of the cartridge 502 with respect to the base 506 can then place the cell 110 into an operational gas-generating mode with respect to electronics 546, and also can optionally occlude a passive gas vent opening (e.g., 522, FIG. 14), and/or seal cone element 536 against conic inner surface 538 (FIG. 13). In FIG. 16, rotation of the cartridge 502 with respect to the base 506 is effected about axial assembly and rotation axis 572.

Embodiment 500 in FIG. 16 also illustrates additional arrangements forming means to vent passive gas generated by the gas cell 110 and thereby to resist spill of delivery material 334 from the delivery device 500 to the environment. First, with reference to FIG. 14, passive gas 578 may be generated by a gas cell 110 when the cell 110 is not in an operational gas-generation configuration. If there is no escape vent path 522, gas 578 flows through aperture 580 and into gas chamber 114. Passive gas 578 is typically created at a very slow rate, but can accumulate in gas chamber 114 to cause undesired spilling of fluid 334 to the local environment. A passive gas-relief valve in one workable embodiment is structured to restrict gas flow there-through to an escape gas flow rate of less than about 0.1 cc per day. In certain cases, a passive gas-relief valve may be structured to restrict gas flow there-through to an escape gas flow rate of between about 0.2 and about 0.5 cc per day.

With reference again to FIG. 16, it is within contemplation to provide a micro-hole, or pore, 590 in penetration through the gas-side rigid portion 102. The pore 590 is effective to vent passive gas generated by the gas cell 110 and thereby to resist spill of delivery material 334 from the delivery device 500 to the environment. A cross-section area, diameter, or other characteristic size of the pore 590 is set to throttle the escape of gas there-through to a rate sufficient to release passive gas, but lower than a rate required to reduce operational pressure caused by a gas cell 110 disposed in an operating gas-generation mode. A workable pore 590 may be formed by laser drilling the rigid portion 102 to create a through-hole having a diameter of about 1 nm.

An alternative means to vent passive gas generated by the gas cell 110 and thereby to resist spill of delivery material 334 from the delivery device 500 to the environment includes window or aperture 594 and its covering gas-permeable membrane 596. The membrane 596 is sized in thickness and permeability to cooperate with a cross-section flow area defined by the aperture 594 such that gas flow through the aperture is restricted to an escape flow rate that permits escape of passive gas, but is lower than a rate required to reduce or compromise operational pressure caused by a gas cell disposed in an operating gas-generation mode. A workable membrane includes polypropylene-based membrane material typically having a thickness between about 1 mil to about 7 mils. One exemplary such membrane material includes ABX 2311, sold by Advanced Barrier Extrusions and having a website at world wide web abxfilms.com. Of course, the cross-section area of window 594 and permeability of membrane 596 are design factors taken into account to form a workable passive gas release vent valve 336.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An orientation independent fluid delivery device, comprising:
   a foundation and a cartridge, the foundation being configured for disposition in association with a surface of a local environment;
   the cartridge comprising:
      a gas chamber comprising a gas-side rigid portion and a gas-side flexible barrier element, wherein the gas-side flexible barrier element is permanently sealed, around a first perimeter of the gas chamber, to the gas-side rigid portion such that gas introduced to the gas chamber is confined between the gas-side flexible barrier element and the gas-side rigid portion;
      a delivery chamber comprising a delivery-side rigid portion and a delivery-side flexible barrier element, wherein the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion, the delivery-side flexible barrier element being oriented adjacent to, and a distinct element from, the gas-side flexible barrier element;
      a gas cell associated with the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element; and
      a delivery aperture to allow a portion of delivery material to escape from the delivery chamber in response to deflection of the delivery-side flexible barrier element in a direction toward the delivery-side rigid portion;
      a retention mechanism to hold the cartridge in installed registration with respect to the foundation and to permit removal of the cartridge from the foundation for replacement of the cartridge with a replacement cartridge; and
      means to vent passive gas generated by the gas cell and thereby to resist unintended discharge of delivery material from the delivery device to the environment, the means to vent passive gas being configured to vent gas at a rate lower than a rate required to compromise operational pressure caused by the gas cell being disposed in an operating gas-generation mode, wherein the means to vent passive gas comprises a passive gas-relief valve disposed in a venting association with the gas chamber to permit discharge of passive gas from inside the gas chamber to the environment.

2. The fluid delivery device according to claim 1, wherein:
   the gas-side flexible barrier element has an outer surface that is in continuous direct contact with the delivery-side flexible barrier element without separation.

3. The fluid delivery device according to claim 1, wherein:
   the passive gas-relief valve comprises a pore passing through the gas-side rigid portion, the pore being sized in a cross-section to throttle gas flow there-through to a rate sufficient to release passive gas, but lower than the rate required to compromise operational pressure caused by a gas cell disposed in an operating gas-generation mode.

4. The fluid delivery device according to claim 1, wherein:
   the passive gas-relief valve comprises an aperture passing through the gas-side rigid portion and a membrane disposed to resist gas flow from the gas chamber through the aperture, the membrane being sized in thickness and permeability to cooperate with a cross-section flow area defined by the aperture such that gas flow through the aperture is restricted to an escape flow rate that permits escape of passive gas, but is lower than the rate required to compromise operational pressure caused by a gas cell disposed in an operating gas-generation mode.

5. The fluid delivery device according to claim 1, wherein:
   the means to vent passive gas comprises a temporary vent path disposed between the gas cell and the gas-side rigid portion, the temporary vent path being formed by structure arranged to be occluded by the act of assembly of the cartridge to the foundation.

6. The fluid delivery device according to claim 1, wherein:
   the passive gas-relief valve is structured to restrict gas flow there-through to an escape gas flow rate of less than 0.1 cc per day.

7. The fluid delivery device according to claim 1, wherein:
   the passive gas-relief valve is structured to restrict gas flow there-through to an escape gas flow rate of between about 0.2 and about 0.5 cc per day.

8. The fluid delivery device according to claim 1, wherein:
   the foundation and the cartridge are structured cooperatively to place the gas cell into operational gas-generating mode by the act of coupling the cartridge to the foundation.

9. The fluid delivery device according to claim 1, further comprising:
   a threshold pressure valve disposed to resist undesired discharge of delivery material from the delivery chamber.

10. The fluid delivery device according to claim 1, further comprising:
    an emanator associated with the delivery aperture, the emanator being structured to absorb delivery material and facilitate distribution and evaporation of the delivery material over a larger area.

11. The fluid delivery device according to claim 1, further comprising:

an absorbent element disposed to facilitate completely filling the delivery chamber with delivery material during manufacture of a device to avoid presence of gas bubbles remaining in the delivery chamber.

12. The fluid delivery device according to claim 1, further comprising:
an overflow emanator chamber associated with the delivery aperture to receive and confine small quantities or even excessive drops of delivery material, the overflow emanator chamber being structured to hold a volume that is at least half the volume held in a full delivery chamber.

13. The fluid delivery device according to claim 1, further comprising:
keeper means to maintain the gas cell in a loose and venting association with the gas-side rigid portion of the cartridge during storage and transport of the cartridge.

14. The fluid delivery device according to claim 1, wherein:
the retention mechanism to hold the cartridge in removable assembled condition with respect to the foundation comprises a toggle clamping mechanism.

15. The fluid delivery device according to claim 1, wherein:
the retention mechanism to hold the cartridge in removable assembled condition with respect to the foundation comprises an inclined plane with a cooperating captured tang and operated by rotation of the cartridge with respect to the foundation.

16. An orientation independent delivery device comprising:
a foundation and a removable cartridge, the foundation being configured for disposition in association with a surface of a local environment and for removable coupling to the cartridge to permit replacement of the cartridge with a replacement cartridge;
a retention mechanism to hold the cartridge in installed registration with respect to the foundation and to permit removal of the cartridge from the foundation for replacement of the cartridge with a replacement cartridge;
the cartridge comprising:
a gas chamber comprising a gas-side rigid portion and a gas-side flexible barrier element, wherein the gas-side flexible barrier element is permanently sealed, around a first perimeter of the gas chamber, to the gas-side rigid portion such that gas introduced to the gas chamber is confined between the gas-side flexible barrier element and the gas-side rigid portion;
a delivery chamber comprising a delivery-side rigid portion and a delivery-side flexible barrier element, wherein the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion, the delivery-side flexible barrier element being oriented adjacent to, and a distinct element from, the gas-side flexible barrier element; with
a self-powered gas cell coupled to the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element; and
a delivery aperture to allow a delivery material to escape from the delivery chamber in response to deflection of the delivery-side flexible barrier element in a direction toward the delivery-side rigid portion; the delivery device further comprising:
means to resist unintended discharge of delivery material from the apparatus to the environment due to change in temperature of the cartridge or as a result of passive gas generation during long-term storage of the cartridge, wherein the means to resist unintended discharge comprises structure forming a vent for passive gas, the vent being configured to resist build-up of pressure in the gas chamber and caused by passive gas released from the gas cell.

17. The device according to claim 16, wherein the means to resist spill comprises:
overflow mitigation structure to mitigate an effect on the local environment of undesired release of fluid from the fluid chamber, the mitigation structure comprising an overflow emanator chamber associated with the delivery aperture to receive and confine spilled drops of delivery material, the emanator storage chamber having a volume at least half as large as the delivery chamber volume.

18. The device according to claim 16, wherein the means to resist spill comprises:
bubble-avoiding structure to resist presence of gas bubbles inside an assembled and loaded material delivery chamber.

* * * * *